(12) United States Patent
Dyer et al.

(10) Patent No.: US 9,429,568 B2
(45) Date of Patent: Aug. 30, 2016

(54) SILAANTHRACENE AS A RED AND NEAR INFRARED SENSOR AND A METHOD TO MANUFACTURE SUCH A SENSOR

(75) Inventors: Daniel Dyer, Carbondale, IL (US); Denise DeAnne Dyer, legal representative, Carbondale, IL (US); Colleen Scott, Carbondale, IL (US); Matthew McCarroll, Carbondale, IL (US); Lichang Wang, Carbondale, IL (US); Narsimha Sattenapally, Carbondale, IL (US); Quinn Best, Carbondale, IL (US)

(73) Assignee: Board of Trustees of Southern Illinois University on Behalf of Southern Illinois University Carbondale, Carbondale, IL (US)

( * ) Notice: Subject to any disclaimer, the term of this patent is extended or adjusted under 35 U.S.C. 154(b) by 0 days.

(21) Appl. No.: 13/993,891

(22) PCT Filed: Dec. 15, 2011

(86) PCT No.: PCT/US2011/065250
§ 371 (c)(1),
(2), (4) Date: Dec. 30, 2014

(87) PCT Pub. No.: WO2012/083064
PCT Pub. Date: Jun. 21, 2012

(65) Prior Publication Data
US 2015/0185209 A1    Jul. 2, 2015

Related U.S. Application Data

(60) Provisional application No. 61/423,974, filed on Dec. 16, 2010.

(51) Int. Cl.
| | |
|---|---|
| *G01N 21/25* | (2006.01) |
| *G01N 33/52* | (2006.01) |
| *G01N 21/64* | (2006.01) |
| *C07F 7/08* | (2006.01) |

(52) U.S. Cl.
CPC .............. *G01N 33/52* (2013.01); *C07F 7/0812* (2013.01); *C07F 7/0818* (2013.01); *G01N 21/6428* (2013.01)

(58) Field of Classification Search
USPC .............................. 436/56, 63, 501, 503, 528
See application file for complete search history.

(56) References Cited

U.S. PATENT DOCUMENTS

2006/0223812 A1* 10/2006 Mandelkow ......... A61K 31/506
                                                                        514/252.11

FOREIGN PATENT DOCUMENTS

CN            100361999           1/2008

OTHER PUBLICATIONS

Kenmoku et al., Development of a Highly Specific Rhodamine-Based Fluorescence Probe for Hypochlorous Acid and Its Application to Real-Time Imaging of Phagocytosis, J. Am. Chem. Soc., vol. 129, No. 23, 129, pp. 7313-7318, 2007.
Fu et al., A Design Concept of Long-wavelength Fluorescent Analogs of Rhodamine Dyes: Replacement of Oxygen with Silicon Atom, Chem. Commun., pp. 1780-1782, 2008.

* cited by examiner

*Primary Examiner* — Pancham Bakshi
(74) *Attorney, Agent, or Firm* — Polsinelli PC

(57) ABSTRACT

Silaanthracene compounds and methods of producing silaanthracene compounds, in particular silaanthracene fluorophores for use as red or near infrared sensors, probes, dyes, and tags are provided.

20 Claims, 6 Drawing Sheets

SILAANTHRACENE AS A RED AND NEAR INFRARED SENSOR AND A METHOD TO MANUFACTURE SUCH A SENSOR

FIELD

The present disclosure is directed to silaanthracene compounds. In particular, the disclosure is directed to silaanthracene fluorophores for use as a red or near infrared sensor.

BACKGROUND

A chemical sensor is a device that produces an analytically useful signal as a result of exposure to an analyte/sample matrix. Fluorescent probes that absorb and emit red NIR radiation have special advantages over their UV or visible counterparts, in particular because red or near infrared (NIR) probes have better performance in biological media, e.g. cells or tissues. The longer wavelength excitation and emission of a red or NIR probe is easily distinguished from biological auto-fluorescence than other types of fluorescent probes. As a result, red or NIR probes perform well at deeper penetration (typically several centimeters) compared to other probes in the biological medium.

Existing fluorophores probes such as rhodamine and fluorescein systems are limited in performance due to the shorter emission wavelengths of these probes. In addition, while fluorescein is FDA approved for limited applications, it is unstable to light, and rhodamine, on the other hand, is banned for its known mutagenic properties, which imposes further limitations on the potential applications of these probes.

A need exists for a fluorophore probe that overcomes the limitations of existing fluorophore systems. Such a fluorophore would have a red or NIR emission wavelength and would further be non-toxic and biocompatible with biological media such as cell or tissue cultures. Applications that would benefit from such a red/NIR non-toxic fluorophore probe include fluorescence microscopy, in vivo imaging, flow cytometry, fluorescence correlation spectroscopy, enzyme-linked immunosorbent assays (ELISA), and dye tracing.

SUMMARY

In an embodiment, a compound comprising formula (I) is provided:

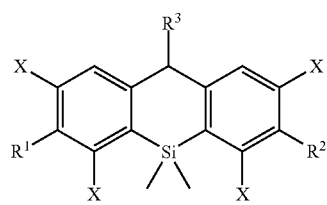

in which $R^1$ is chosen from amino and hydroxy; $R^2$ is chosen from amino, imino, hydroxy, and keto; X is chosen from hydrogen or halogen; and $R^3$ is chosen from hydrogen, keto, isoindolinones, substituted isoindolinones, isobenzofuranones, substituted isobenzofuranones, tetrahydroisobenzothiophenes, substituted tetrahydroisobenzothiophenes, alkyl, substituted alkyl, aryl, substituted aryl, benzyl, and substituted benzyl, provided that $R^3$ is not hydrogen, phenyl, p-methylphenyl, p-methyl-2N-phenyl, p-methoxyphenyl, p-chlorophenyl, or o-chlorophenyl when $R^1$ is amino, $R^2$ is imino and X is hydrogen.

In another embodiment, a chemical sensor/probe compound is provided comprising Formula (I):

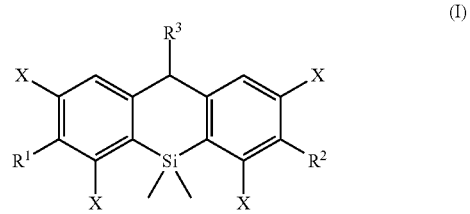

in which X is chosen from hydrogen or halogen; $R^1$ is chosen from amino and hydroxy; $R^2$ is chosen from amino, imino, hydroxy, and keto; and $R^3$ is chosen from hydrogen, keto, isoindolinones, substituted isoindolinones, isobenzofuranones, substituted isobenzofuranones, tetrahydroisobenzothiophenes, substituted tetrahydroisobenzothiophenes, alkyl, substituted alkyl, aryl, substituted aryl, benzyl, and substituted benzyl, provided that $R^3$ is not hydrogen, phenyl, p-methylphenyl, p-methyl-2N-phenyl, p-methoxyphenyl, p-chlorophenyl, or o-chlorophenyl when $R^1$ is amino, $R^2$ is imino and X is hydrogen. The chemical sensor/probe compound produces one or more analytically useful signals when contacted with at least one analyte.

In an additional embodiment, a dye/tag compound is provided comprising Formula (I):

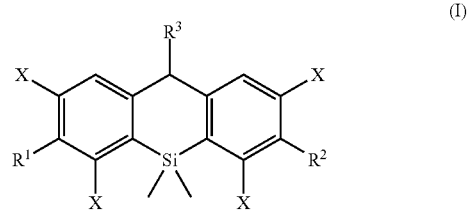

in which X is chosen from hydrogen or halogen; $R^1$ is chosen from amino and hydroxy; $R^2$ is chosen from amino, imino, hydroxy, and keto; $R^3$ is chosen from hydrogen, keto, isoindolinones, substituted isoindolinones, isobenzofuranones, substituted isobenzofuranones, tetrahydroisobenzothiophenes, substituted tetrahydroisobenzothiophenes, alkyl, substituted alkyl, aryl, substituted aryl, benzyl, and substituted benzyl, provided that $R^3$ is not hydrogen, phenyl, p-methylphenyl, p-methyl-2N-phenyl, p-methoxyphenyl, p-chlorophenyl, or o-chlorophenyl when $R^1$ is amino, $R^2$ is imino and X is hydrogen. The dye/tag compound is mixed with or attached to an entity, and one or more analytically useful signals produced by the dye/tag compound are monitored.

Additional objectives, advantages and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
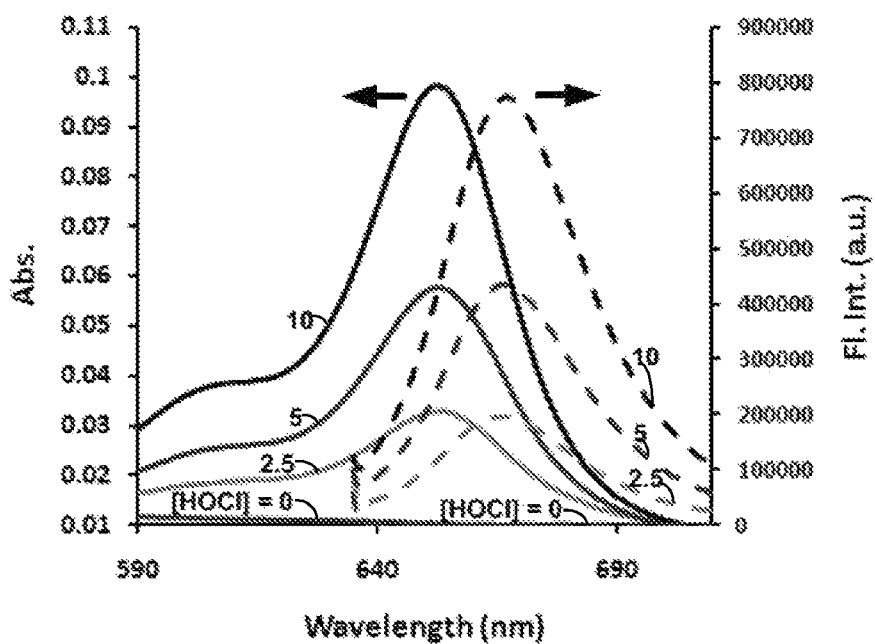
FIG. 1 is a spectrum of the absorbance and emission intensity of a silaanthracene fluorophore probe at various concentrations of HOCl.

The invention relates to the synthesis and sensing capabilities of highly functionalized silaanthracene fluorophores generally containing nitrogen or oxygen in the 2 and 7 positions of the ring. In various embodiments, the functionalized silaanthracene fluorophores absorb and emit red and near-infrared radiation. In an embodiment, the functionalized silaanthracene fluorophores may be used as chemical sensors/probes, in which the functionalized silaanthracene fluorophores may produce an analytically useful signal as a result of exposure to an analyte. In another embodiment, the functionalized silaanthracene fluorophores may be attached to an entity and used as tag to track the entity. Embodiments of the functionalized silaanthracene fluorophores, methods of producing the functionalized silaanthracene fluorophores, and uses of the functionalized silaanthracene fluorophores are described in detail herein below.

(I) Functionalized Silaanthracene Fluorophores

One aspect of the present invention is the provision of functionalized silaanthracene fluorophores.

(a) Compounds Comprising Formula (I)

In one embodiment, the functionalized silaanthracene fluorophore may be a compound comprising Formula (I):

(I)

in which $R^1$ is chosen from amino and hydroxy; $R^2$ is chosen from amino, imino, hydroxy, and keto; X is chosen from hydrogen or halogen; and $R^3$ is chosen from hydrogen, keto, isoindolinones, substituted isoindolinones, isobenzofuranones, substituted isobenzofuranones, tetrahydroisobenzothiophenes, substituted tetrahydroisobenzothiophenes, alkyl, substituted alkyl, aryl, substituted aryl, benzyl, and substituted benzyl, provided that $R^3$ is not hydrogen, phenyl, p-methylphenyl, p-methyl-2N-phenyl, p-methoxyphenyl, p-chlorophenyl, or o-chlorophenyl when $R^1$ is amino, $R^2$ is imino and X is hydrogen.

Specific examples of the substituent group $R^3$ are summarized in Table 1 below:

TABLE 1

$R^3$ Substituents for Functionalized Silaanthracene Compounds

| Substituent Group | Formula |
|---|---|
| 1 | |
| 2 | |
| 3 | |
| 4 | |
| 5 | |
| 6 | |
| 7 | |

TABLE 1-continued
R³ Substituents for Functionalized Silaanthracene Compounds
| Substituent Group | Formula |
|---|---|
| 8 | 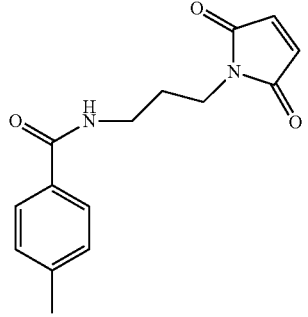 [SMILES: Cc1ccc(C(=O)NCCCN2C(=O)C=CC2=O)cc1] |
| 9 | 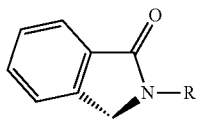 |
| 10 | 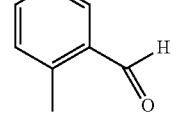 |
| 11 | 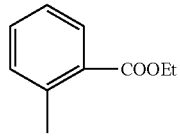 |
| 12 | 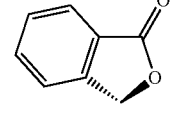 |
| 13 | 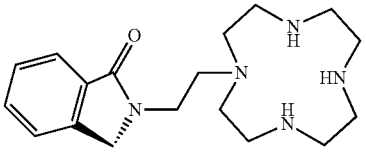 |
| 14 | 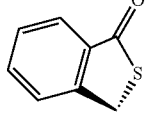 |
| 15 | 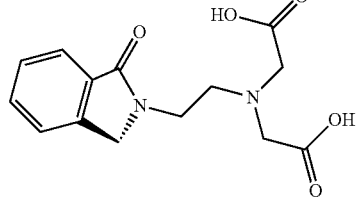 |
| 16 | 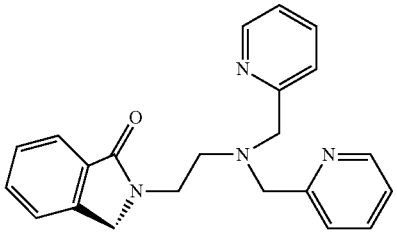 |
| 17 | 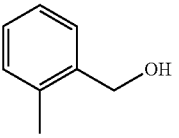 |
| 18 | 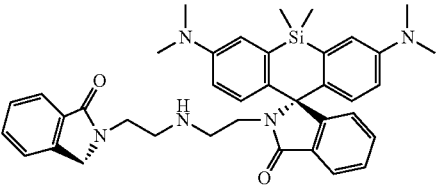 |
| 19 | 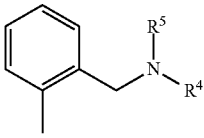 |
| 20 | 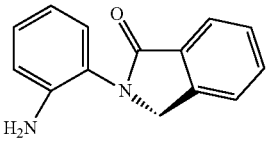 |
| 21 | 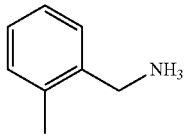 |
| 22 | 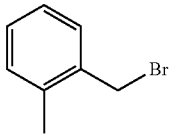 |
| 23 | 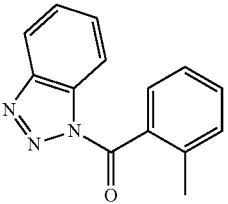 [SMILES: Cc1ccccc1C(=O)n1nnc2ccccc21] |

(b) Compounds Comprising Formula (II)

In another embodiment, the functionalized silaanthracene fluorophore may be a compound comprising Formula (II):

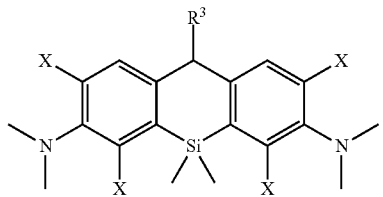

(II)

in which X is chosen from hydrogen or halogen; and $R^3$ is chosen from hydrogen, keto, isoindolinones, substituted isoindolinones, isobenzofuranones, substituted isobenzofuranones, tetrahydroisobenzothiophenes, substituted tetrahydroisobenzothiophenes, or any of the specific examples of $R^3$ groups summarized in Table 1 herein.

Specific examples of compounds comprising Formula (II) are provided in Table 2 below:

TABLE 2

Examples of Silaanthracene Compounds Comprising Formula (II)

| Compound | Formula |
|---|---|
| 1 | |
| 2 | |
| 3 | |
| 4 | |
| 5 | |
| 6 | |
| 7 | |
| 8 | |
| 9 | |

TABLE 2-continued

Examples of Silaanthracene Compounds Comprising Formula (II)

| Compound | Formula |
|---|---|
| 10 | 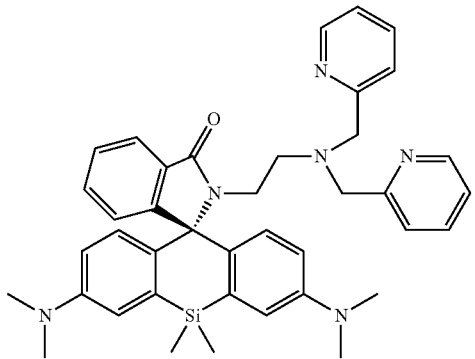 |
| 11 | 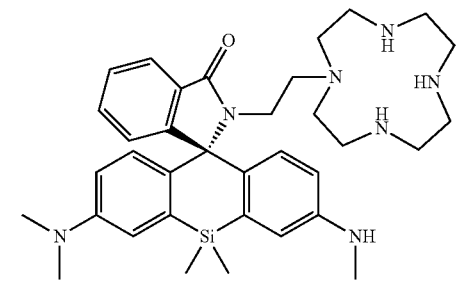 [SMILES: CNc1ccc2c(c1)[Si](C)(C)c1cc(N(C)C)ccc1[C@@]21c2ccccc2C(=O)N1CCN1CCNCCNCCNCC1] |

(c) Compounds Comprising Formula (III)

In an additional embodiment, the functionalized silaanthracene fluorophore may be a compound comprising Formula (III):

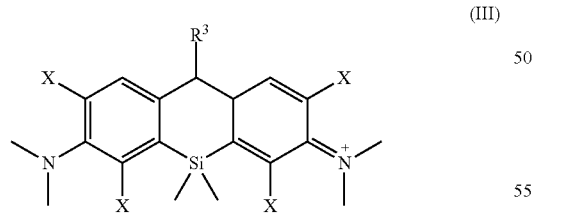

in which X is chosen from hydrogen or halogen; and $R^3$ is chosen from alkyl, substituted alkyl, benzyl, substituted benzyl, and any of the specific examples of $R^3$ groups summarized in Table 1 herein, provided that $R^3$ is not hydrogen, phenyl, p-methylphenyl, p-methyl-2N-phenyl, p-methoxyphenyl, p-chlorophenyl, or o-chlorophenyl when X is hydrogen.

Specific examples of compounds comprising Formula (III) are provided in Table 3 below:

TABLE 3

Examples of Silaanthracene Compounds Comprising Formula (III)

| Compound | Formula |
|---|---|
| 12 | 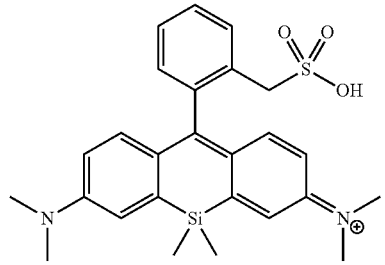 |
| 13 | 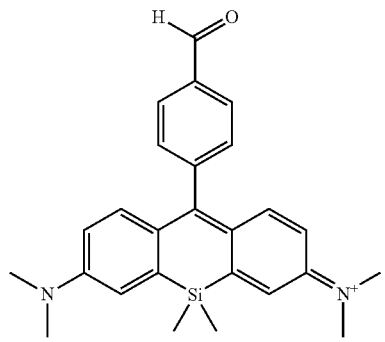 |
| 14 | 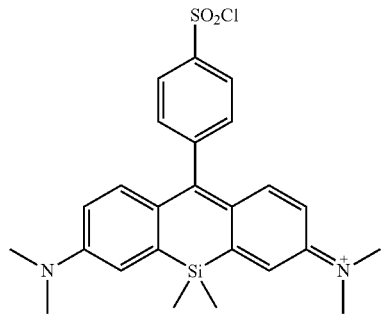 |
| 15 | 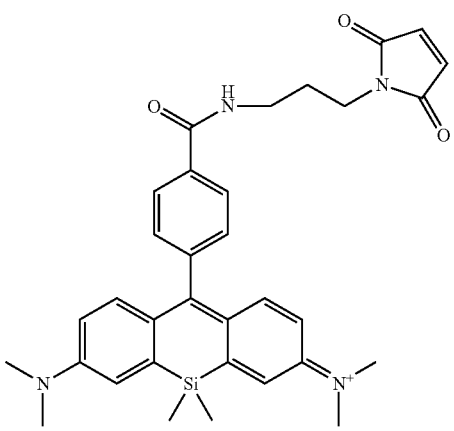 [SMILES: CN(C)c1ccc2c(c1)[Si](C)(C)C1=CC(=[N+](C)C)C=CC1=C2c1ccc(C(=O)NCCCN2C(=O)C=CC2=O)cc1] |

TABLE 3-continued

Examples of Silaanthracene Compounds Comprising Formula (III)

| Compound | Formula |
|---|---|
| 16 | (structure) |
| 17 | (structure) |
| 18 | (structure) |
| 19 | (structure) |
| 20 | (structure) |
| 21 | (structure) |
| 22 | (structure) |
| 23 | (structure) |
| 24 | (structure) |

(d) Compounds Comprising Formula (IV)

In another additional embodiment, the functionalized silaanthracene fluorophore may be a compound comprising Formula (IV):

(IV)

in which X is chosen from hydrogen or halogen; and $R^3$ is chosen from hydrogen, keto, isoindolinones, substituted isoindolinones, isobenzofuranones, substituted isobenzofuranones, tetrahydroisobenzothiophenes, substituted tetrahydroisobenzothiophenes, and any of the specific examples summarized in Table 1 herein.

Table 4 provides formulas of specific examples of compounds comprising Formula (IV):

TABLE 4

Examples of Silaanthracene Compounds Comprising Formula (IV)

| Compound | Formula |
|---|---|
| 25 | |
| 26 | |
| 27 | |
| 28 | |
| 29 | |
| 30 | |

TABLE 4-continued

Examples of Silaanthracene Compounds Comprising Formula (IV)

| Compound | Formula |
|---|---|
| 31 | |
| 32 | |
| 33 | |

(e) Compounds Comprising Formula (V)

In one further additional embodiment, the functionalized silaanthracene fluorophore may be a compound comprising Formula (V):

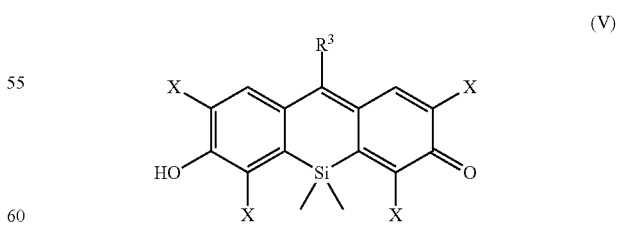

(V)

in which X is chosen from hydrogen or halogen, $R^3$ is chosen from hydrogen, alkyl, substituted alkyl, aryl, substituted aryl, benzyl, substituted benzyl, and any of the specific examples summarized in Table 1 herein.

Table 5 provides formulas of specific examples of compounds comprising Formula (V):

TABLE 5

Examples of Silaanthracene Compounds Comprising Formula (V)

| Compound | Formula |
|---|---|
| 34 | |
| 35 | |
| 36 | |
| 37 | |
| 38 | |

TABLE 5-continued

Examples of Silaanthracene Compounds Comprising Formula (V)

| Compound | Formula |
|---|---|
| 39 | |
| 40 | |
| 41 | |
| 42 | |

TABLE 5-continued

Examples of Silaanthracene Compounds Comprising Formula (V)

| Compound | Formula |
|---|---|
| 43 | 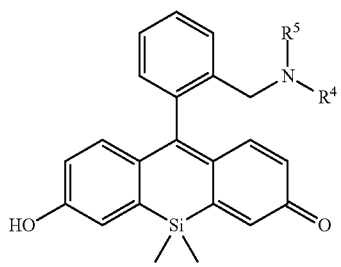 |
| 44 | 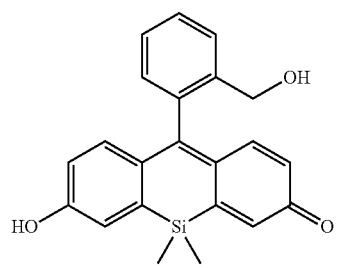 [SMILES: C[Si]1(C)C2=CC(=O)C=CC2=C(c2ccccc2CO)c2ccc(O)cc21] |
| 45 | 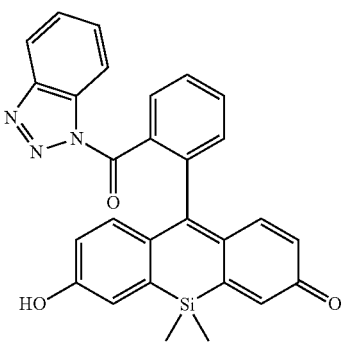 [SMILES: C[Si]1(C)C2=CC(=O)C=CC2=C(c2ccccc2C(=O)n2nnc3ccccc32)c2ccc(O)cc21] |
| 46 | 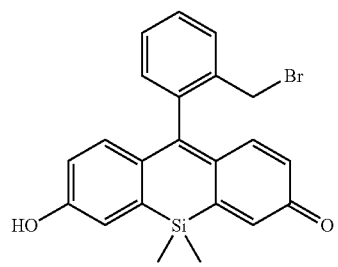 [SMILES: C[Si]1(C)C2=CC(=O)C=CC2=C(c2ccccc2CBr)c2ccc(O)cc21] |
| 47 | 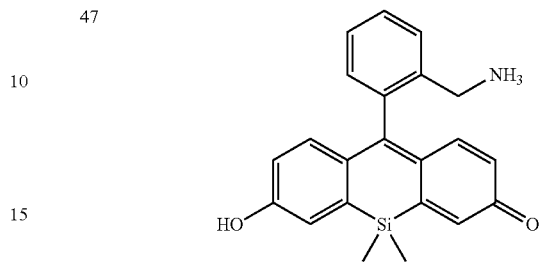 |

(II) Synthesis of Functionalized Silaanthracene Fluorophores

One aspect of the present invention is the provision of a method of producing functionalized silaanthracene fluorophores. An example of a synthetic scheme for various silaanthracene compounds is described below:

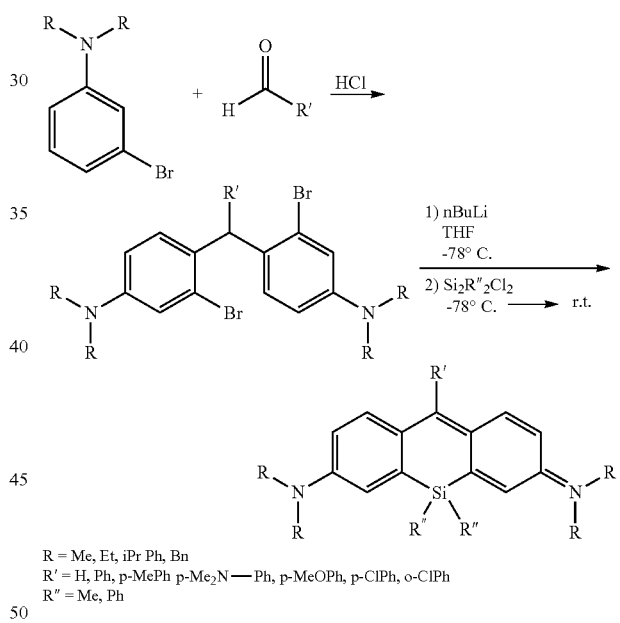

R = Me, Et, iPr Ph, Bn
R' = H, Ph, p-MePh p-Me$_2$N—Ph, p-MeOPh, p-ClPh, o-ClPh
R'' = Me, Ph (a) Compounds Comprising Formula (II)

In one embodiment, a synthetic scheme for producing silaanthracene compounds comprising Formula (II) is as follows:

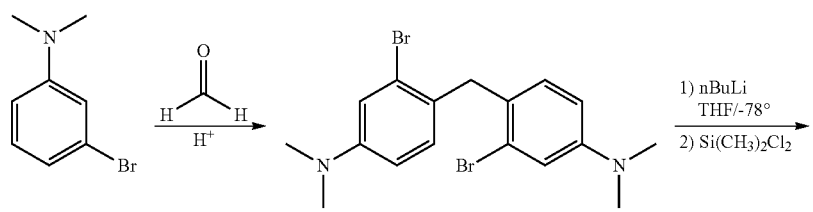

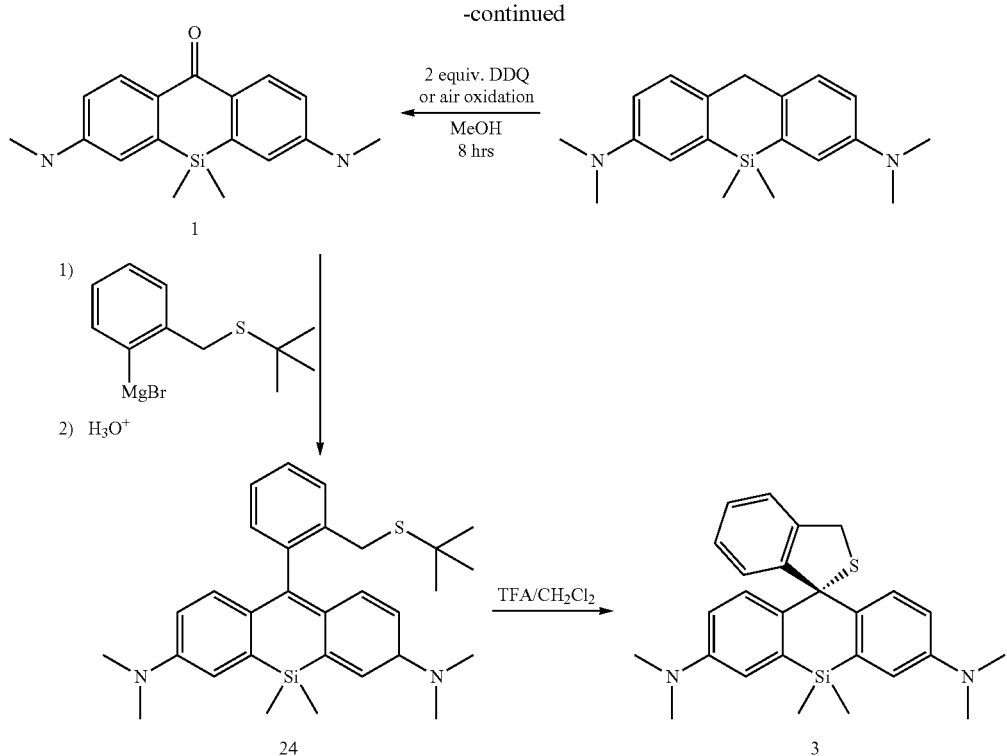

In this synthetic scheme, compound 1 represents a key intermediate compound from which the compounds comprising Formula (I) may be synthesized. For example, in this synthetic scheme, compounds 24 and 3 are synthesized from compound 1.

(b) Compounds Comprising Formula (III)

In one embodiment, a silaanthracene compound comprising Formula (III) may be synthesized from a silaanthracene compound comprising Formula (II). For example, compound 12 may be synthesized from compound 3 using the following scheme:

In another embodiment, a silaanthracene compound comprising Formula (III) may be synthesized from key intermediate compound 1. For example, compound 3 may be synthesized from compound 1 using the following scheme:

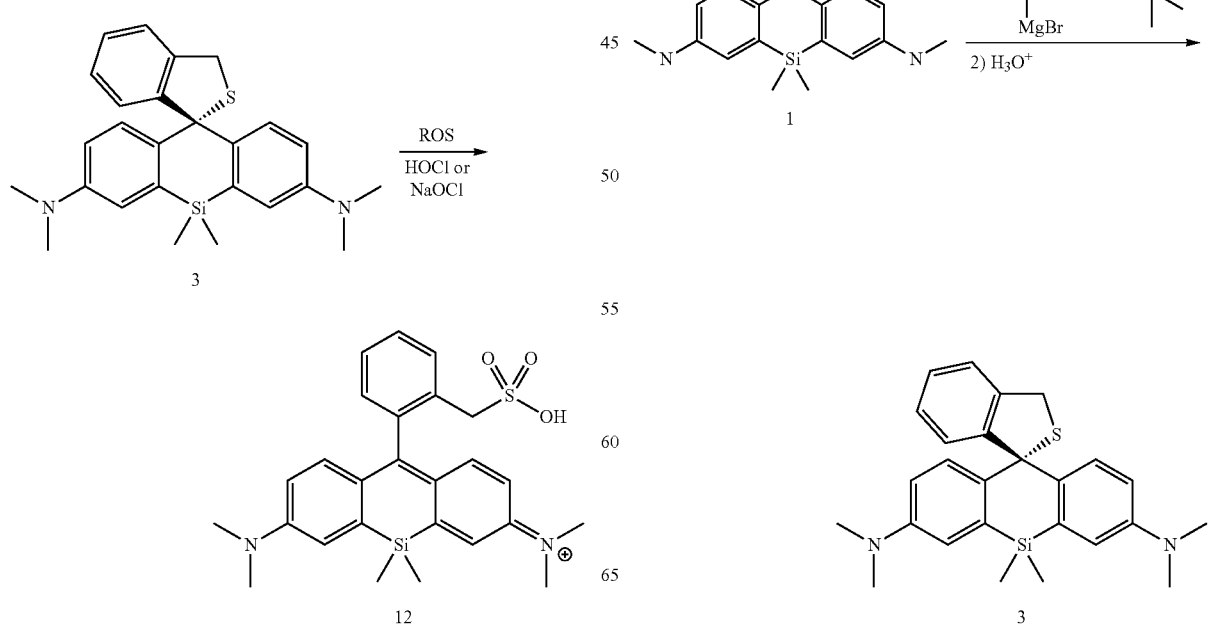

(c) Compounds Comprising Formula (IV)

In one embodiment, a synthetic scheme for producing silaanthracene compounds comprising Formula (IV) is as follows:

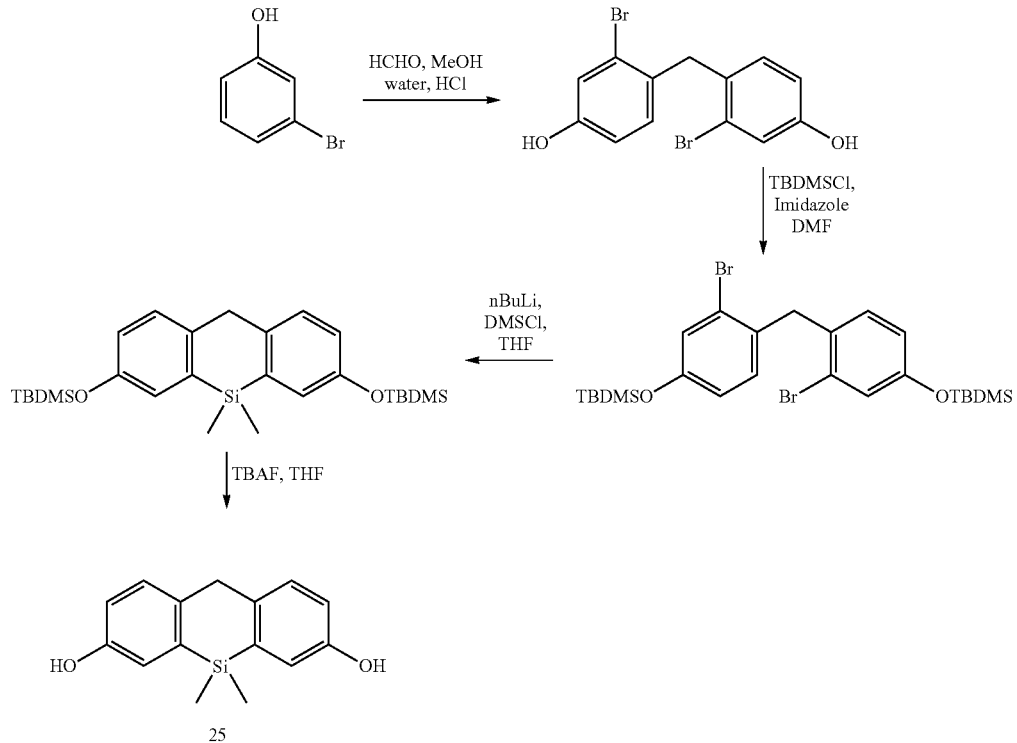

(c) Compounds Comprising Formula (V)

In one embodiment, a synthetic scheme for producing silaanthracene compounds comprising Formula (IV) is as follows:

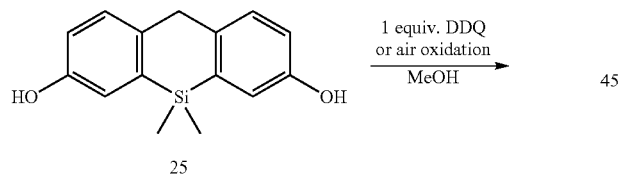

-continued

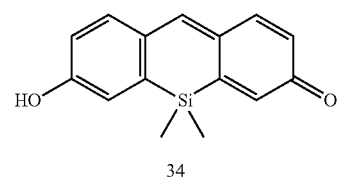

In another embodiment, a synthetic scheme for producing silaanthracene compounds comprising Formula (V) is as follows:

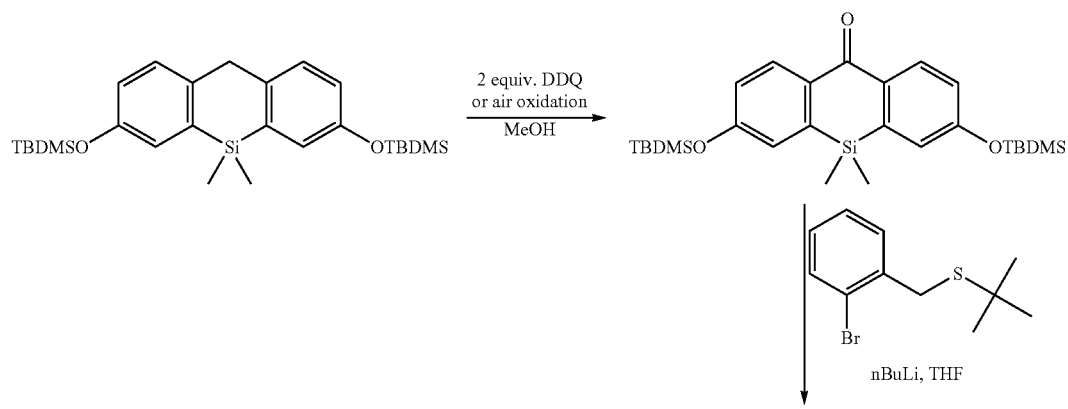

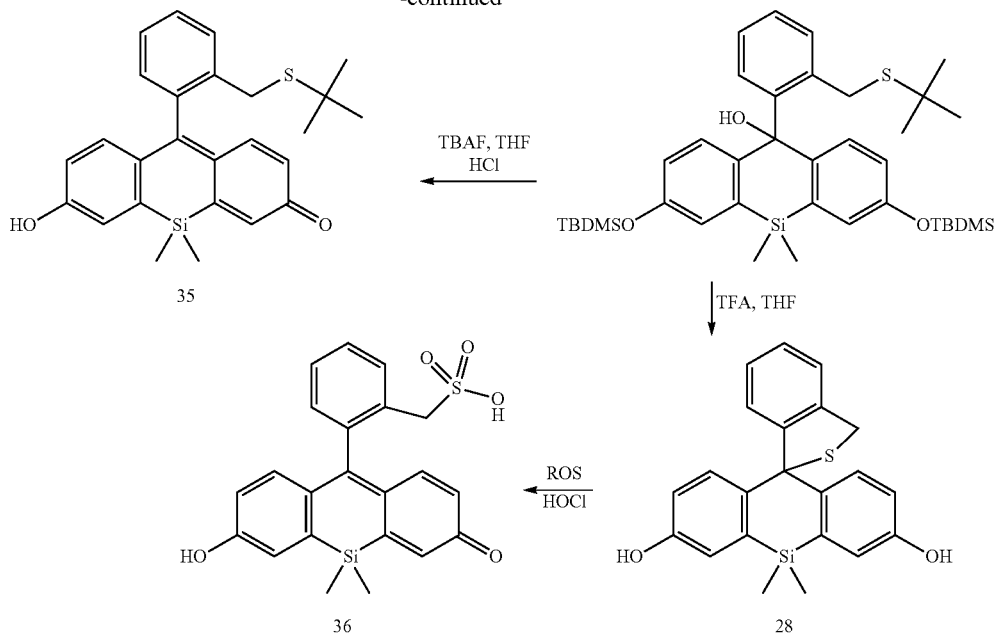

(III) Uses of Functionalized Silaanthracene Fluorophores

The silaanthracene compounds described herein above typically possess the useful ability to absorb and emit light in the red and near-infrared range. Due to this ability, the silaanthracene compounds described herein may be used in a variety of applications, including but not limited to chemical sensors/probes, tags, and dyes. The silaanthracene compounds may be used as chemical sensors/probes, tags, and/or dyes in any known analytical method. Non-limiting examples of analytical methods in which the silaanthracene compounds may be used as signal compounds include Fluorescence Microscopy, in vivo Imaging, Flow Cytometry, Fluorescence Correlation Spectroscopy, Enzyme-linked Immunosorbent Assay (ELISA), and dye tracing of moving objects and liquids in a variety of contexts. The silaanthracene compounds may be particularly useful in biological applications because the longer excitation and emission wavelengths of the silaanthracene compounds typically penetrate deeper into biological tissues and other biological media compared to existing compounds. In addition, the wavelengths of excitation and emission of the silaanthracene compounds are significantly different from the biological auto-fluorescence wavelengths. The silaanthracene compounds are also typically non-toxic in use.

(a) Silaanthracene Chemical Sensors/Probes

In an aspect, the silaanthracene compounds may be used as chemical sensors/probes, defined herein as including any compound capable of producing an analytically useful signal as a result of exposure to, or contact with, an analyte or sample matrix.

As a chemical sensor/probe, the silaanthracene compounds may be contacted with at least one analyte, and an analytically useful signal may be produced upon contact with the at least one analyte. Non-limiting examples of types of analytes amenable to chemical sensing or probing using the silaanthracene compounds include cells; subcellular structures such as DNA and proteins; chemical compounds; chemical conditions such as temperature, pressure, pH, concentration of compounds; and any combination thereof.

Non-limiting examples of chemical compounds include hydrogen ions, metal ions such as alkali metal ions, active oxygen species such as nitrogen monoxide, a hydroxy radical, a singlet oxygen, a superoxide, a peroxy nitrite, and a hypochlorous acid.

Upon contact with a sample containing one or more analytes, a silaanthracene compound may produce one or more analytically useful signals. In an aspect, two or more silaanthracene compounds may be contacted with a sample in order to signal a characteristic of at least one analyte in the sample. Non-limiting examples of analytically useful signals include absorption of light at a wavelength characteristic of the silaanthracene compound, emission of light at a wavelength characteristic of the silaanthracene compound, a characteristic color change in solution, and any combination thereof. In an aspect, the analytically useful signal may be the intensity of light emitted at a wavelength characteristic of the silaanthracene compound. In another aspect, the analytically useful signal may be a mathematical combination of two or more intensities of light emitted at two or more wavelengths characteristic of the silaanthracene compound.

The useful analytical signal may include light emitted by a silaanthracene compound in response to an excitatory light pulse delivered at a predetermined wavelength. One or more different excitatory wavelengths may be used to induce the emission of light at one or more emission wavelengths. In an aspect, the intensity of light emissions induced by two or more different excitatory wavelengths, the emission wavelengths of light emissions induced by two or more different excitatory wavelengths, or any combination thereof, may be mathematically combined and used as a useful analytical signal.

Any known method of mathematically combining absorption intensities, emission intensities, absorption wavelengths, emission wavelengths, or any combination thereof may be used. Non-limiting examples of mathematical combinations of signals include signal sums, signal differences, signal products, signal ratios, signal integrations, signal rates, and any combination thereof. For example, a silaanthracene compound may produce a ratiometric signal in which the analytically useful signal is the ratio of the intensities of light emission at two different wavelengths.

In an aspect, the analytically useful signal may be produced in response to the sensing of a single aspect of the analyte. For example, the signal may be produced in response to sensing the presence of a particular analyte, but may not change in response to different concentrations or variations in structure of the analyte. In another aspect, variations of the analytically useful signal may be produced in response to the sensing of two or more aspects of the analyte, or the sensing of two or more analytes. For example, the intensity of light emitted may increase or decrease in response to changes in the concentration of an analyte. As another example, the emission wavelength produced by a silaanthracene compound may shift in response to variations in the structure, concentration, or any other characteristic of one or more analytes contacted with the silaanthracene compound.

In another aspect, two or more signals may be produced by a single silaanthracene compound in response to contact with two or more different analytes. In this aspect, one of the two or more signals may be produced independently of the other signals, or the production of one signal may be dependent upon the production of one or more of the other signals. For example, a silaanthracene compound may emit light at a characteristic wavelength upon contact with an analyte compound, and may further take on a characteristic color in solution depending on the pH of the solution.

b) Silaanthracene Dyes and Tags

In another aspect, a silaanthracene compound as described herein above may be used as a dye. In this aspect, the silaanthracene compound may be contacted with an entity and one or more analytically useful signals described herein above may be detected. The analytically useful signals may be detected in a continuous or non-continuous manner in various aspects. For example, a silaanthracene compound may be mixed with at least a portion of a liquid, and an analytically useful signal such as emission at a characteristic wavelength may be monitored continuously in order to track the position and movements of the liquid. In this example, the analytically useful signal may be used to monitor flow phenomena including, but not limited to, diffusion, convection, flow speed, flow turbulence, and any combination thereof.

In another aspect, a silaanthracene compound as described herein above may be used as a tag. In this aspect, the silaanthracene compound may be attached to an entity, and one or more analytically useful signals described herein above may be detected. Non-limiting examples of entities suitable for attachment to a silaanthracene compound in this aspect include peptides, proteins, other biomolecules, and biological cells such as blood cells of a particular type or bacteria cells, and any other biological or non-biological entity. The analytically useful signals may be detected in a continuous or non-continuous manner in various aspects. For example, a silaanthracene compound with an affinity for attachment to a particular type of cell such as a cancer cell may be injected into a tissue, and an analytically useful signal such as emission at a characteristic wavelength may be detected in a single instance to determine the location of the tagged cancer cells within the tissue. In another example, a silaanthracene compound with an affinity for attachment to a particular blood cell type such as an activated leukocyte associated with an immune response may be injected into the bloodstream of a patient, and the concentration of the tagged activated leukocyte may be continuously monitored using a known method such as in vivo flow cytometry.

Other non-limiting examples of applications of the silaanthracene compounds are provided in detail herein below.

EXAMPLES

The following examples illustrate various aspects of the invention.

Example 1

Assessment of a Silaanthracene Compound as a Hypochlorous Acid Sensor

To demonstrate the ability of a silaanthracene compound to function as a hypochlorous acid (HOCl) sensor at extremely low concentrations, the following experiments were conducted. A solution of compound 3 from Table 2 herein was formed at a concentration of 0.5 µM and at a pH of 7.4. HOCl was added to the solution at concentrations ranging up to 2 µM and the fluorescence of the resulting solutions was measured after exposure to an excitatory light pulse of 655 nm.

Figure 2:
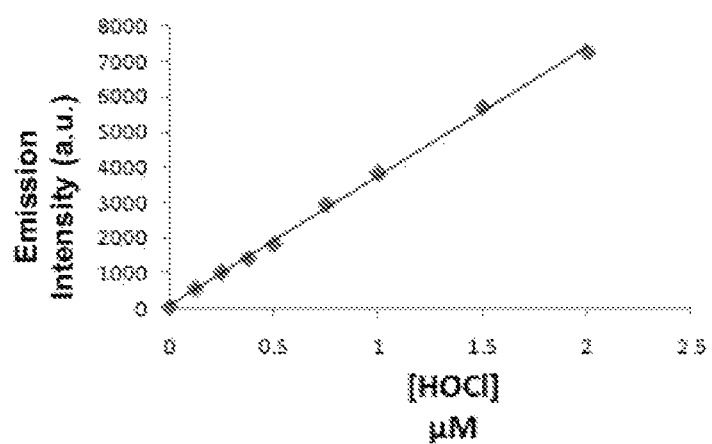
FIG. 2 is a graph summarizing the linear response of a silaanthracene fluorophore probe at a wavelength of 663 nm as a function of HOCl concentration.

FIG. 1 summarizes the spectra of the fluorescence intensity of compound 3 after exposure to HOCl. At all HOCl concentrations, the peak emission intensities were observed at a wavelength of 663 nm. FIG. 2 summarizes the intensity of the fluorescence at 663 nm of a series of HOCl solutions as a function of the HOCl concentration of each solution, demonstrating a linear relationship through the range of HOCl concentrations tested.

Example 2

Assessment of a Second Silaanthracene Compound as a Hypochlorous Acid Sensor

To demonstrate the ability of a second silaanthracene compound to function as a hypochlorous acid (HOCl) sensor at extremely low concentrations, the following experiments were conducted. A solution of compound 29 from Table 5 herein was formed at a concentration of 0.5 µM and at a pH of 7.4. HOCl was added to the solution at concentrations ranging up to 5 µM and the fluorescence of the resulting solutions was measured after exposure to an excitatory light pulse of 580 nm.

Figure 3A:
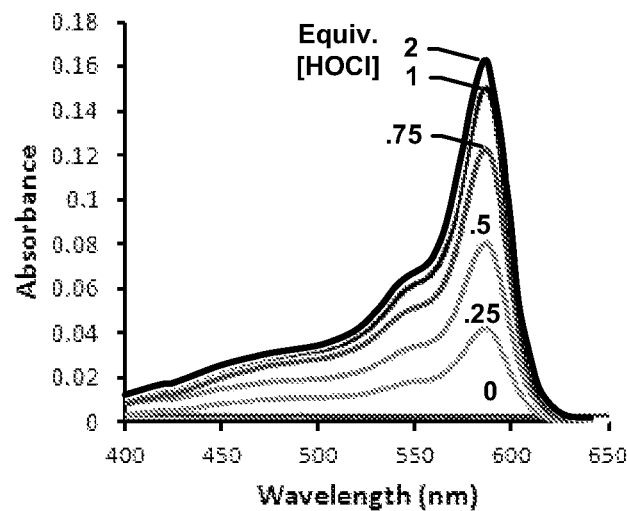
FIG. 3A is a spectrum of the absorbance intensity of a silaanthracene fluorophore probe at various concentrations of HOCl.
Figure 3B:
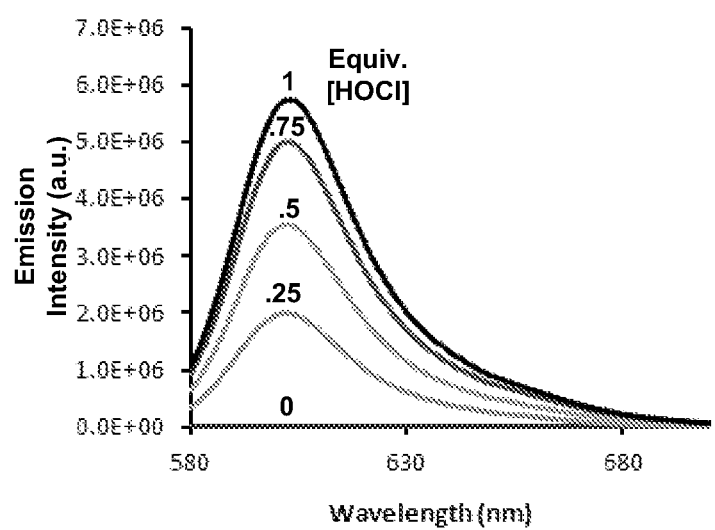
FIG. 3B is a spectrum of the emission intensity of a silaanthracene fluorophore probe at various concentrations of HOCl when excited at wavelength of 570 nm.
Figure 3C:
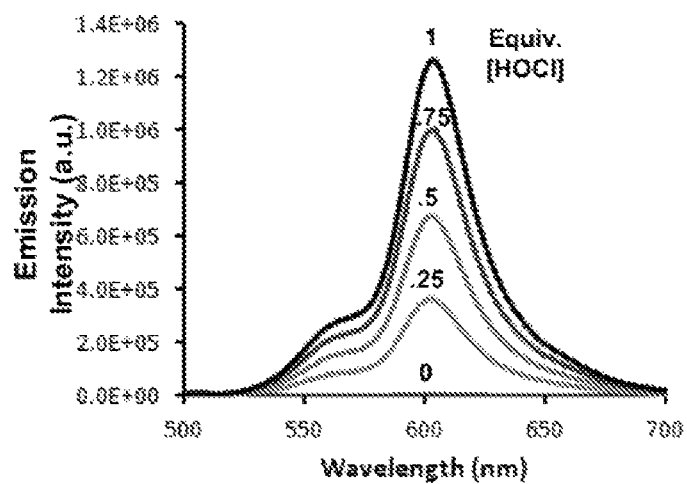
FIG. 3C is a spectrum of the emission intensity of a silaanthracene fluorophore probe at various concentrations of HOCl when excited at wavelengths of 430 nm.
Figure 3D:
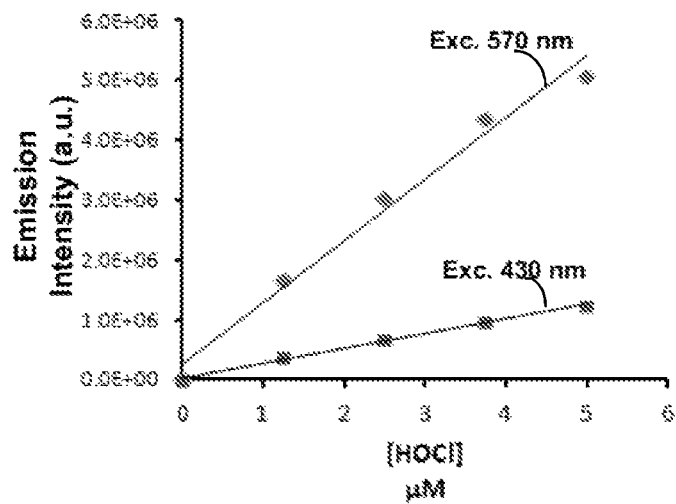
FIG. 3D is a graph summarizing the linear response of a silaanthracene fluorophore probe excited at wavelengths of 430 and 605 nm, as a function of HOCl concentration.

FIG. 3A summarizes the absorbance spectra of compound 29, which had a maximum absorbance wavelength $\lambda_{max}$ of 590 nm. FIG. 3B and FIG. 3C summarize the emission spectra when excited at wavelengths of 570 nm and 430 nm respectively. At all HOCl concentrations, the peak emission intensities were observed at a wavelength of 605 nm when excited at 570 nm. There is a shoulder peak at 570 nm when excited at 430 nm. FIG. 3D summarizes the intensity of the fluorescence at 605 nm and 570 nm for a series of HOCl solutions as a function of the HOCl concentration of each solution, demonstrating a linear relationship through the range of HOCl concentrations tested.

Example 3

Assessment of a Silaanthracene Compound as a Ratiometric Sensor for Hypochlorous Acid and pH To demonstrate the ability of a silaanthracene compound to function as a ratiometric sensor for hypochlorous acid (HOCl) and for pH at extremely low concentrations, the following experiments were conducted. A solution of compound 29 from Table 4 herein was dissolved in a series of phosphate buffer or citrate/phosphate buffer solutions using 0.5% DMF for dissolution. The pH level of each sample solution was checked using a digital pH meter (Accumet, AB15) equipped with a glass electrode (Accumet, pH/ATC Calomel) to confirm the pH of each sample solution. After recording the pH of a sample solution, 20 mL of the sample solution was stirred in a 50 mL beaker to saturate the sample solution with oxygen. Small aliquots from a dilute HOCl solution were then added to the sample solution. After the addition of each HOCl aliquot, the sample solution was stirred for approximately 45 seconds and then the UV-Vis and fluorescence of the sample solution was measured using a quartz cuvette with fluorescence excitations at 570 nm and 430 nm. The concentration of the NaOCl solution was determined by using a standardized sodium thiosulfate solution.

Figure 4A:
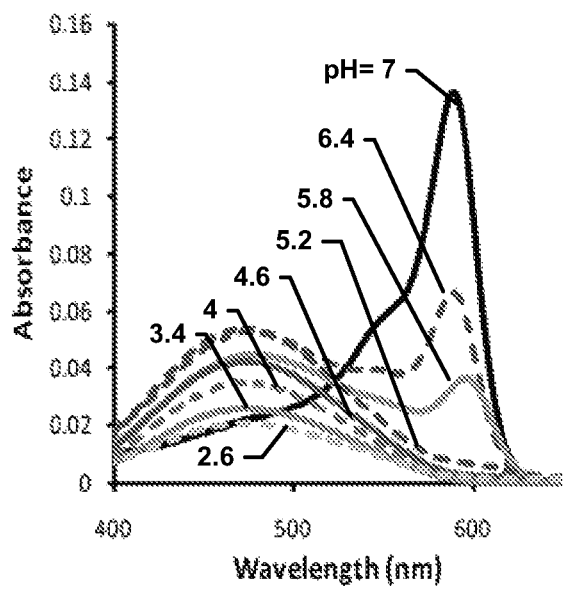
FIG. 4A is a spectrum of the absorbance intensity of a silaanthracene fluorophore probe with 4 equivalents of HOCl concentrations at various sample pH levels.
Figure 4B:
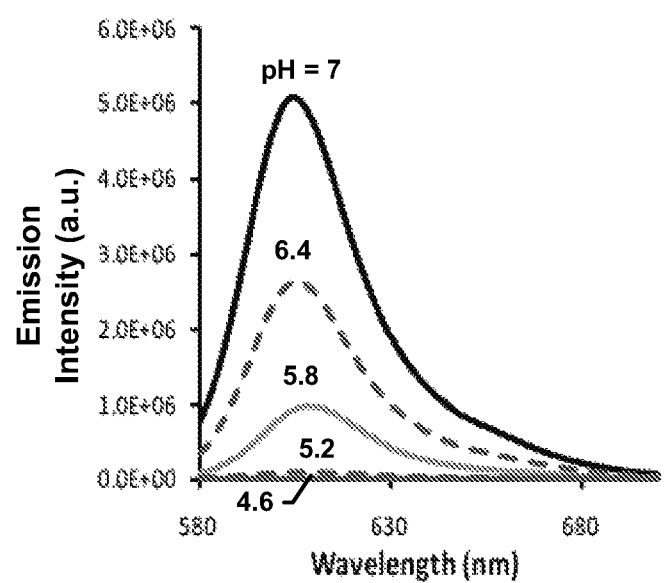
FIG. 4B is a spectrum of the emission intensity of a silaanthracene fluorophore probe with 4 equivalents of HOCl concentrations at various sample pH levels when excited at wavelength of 570 nm.
Figure 4C:
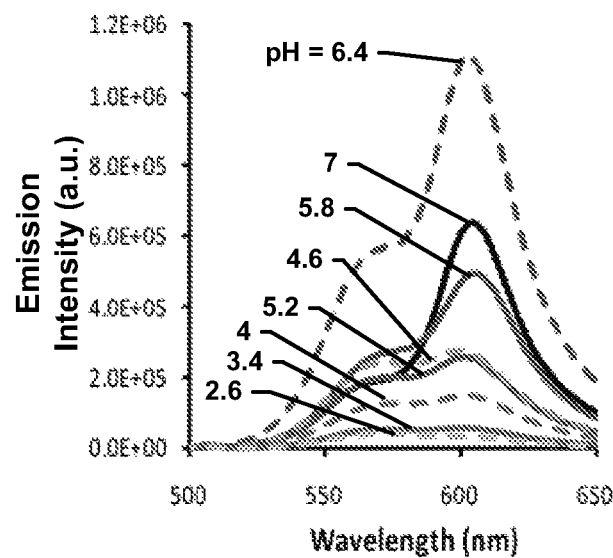
FIG. 4C is a spectrum of the emission intensity of a silaanthracene fluorophore probe with 4 equivalents of HOCl concentrations at various sample pH levels when excited at wavelength of 430 nm.
Figure 4D:
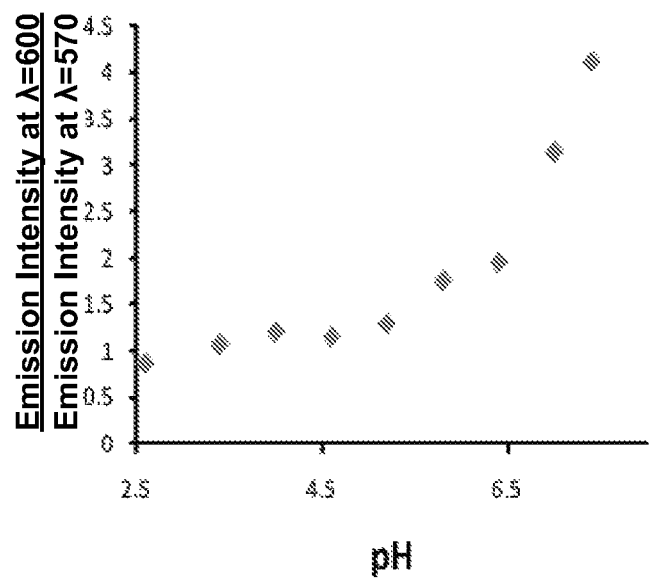
FIG. 4D is a graph summarizing the ratiometric response of a silaanthracene fluorophore probe as a function of the pH concentration of the samples.

FIG. 4A summarizes the absorbance spectra of 5 μM solutions of compound 29 with 4 equivalents of HOCl at various pH levels. FIG. 4B summarizes the emission spectrum of compound 29 with 4 equivalents of HOCl at various pH when excited at 570 nm. FIG. 4C summarizes the emission spectrum of compound 29 with 4 equivalents of HOCl at various pH when excited at 430 nm.

At all HOCl concentrations excited at 430 nm, a first emission intensity peak was observed at an emission wavelength of 570 nm, and a second more intense peak was observed at an emission wavelength of 600 nm, as shown in FIG. 4. These two emission peaks changed intensity as a function of the pH of the sample solution, resulting in a ratiometric response to changes in the pH of the sample solution. The ratio of the emission intensity at 600 nm and the emission intensity at 570 nm varied as a monotonically increasing function of the sample pH, as summarized in FIG. 4D.

Example 4

Assessment of a Silaanthracene Compound as an Assay for HOCl and pH

To demonstrate the ability of a silaanthracene compound to function as a pool kit sensor for hypochlorous acid (HOCl) and pH at extremely low concentrations, the following experiments were conducted. In a 5 mL volumetric flask, sample solutions were produced containing HOCl at concentrations ranging from 0-3 ppm dissolved in 0.1 M citrate/phosphate buffer solution ranging in pH from 5.0-7.0. To these sample solutions, 200 μL of a stock solution containing compound 29 in DMF at a concentration of 1.56 μM was added. After the addition of the stock solution, UV-Vis and fluorescence measurements were taken of each sample solution. Color photographs of each sample solution were also taken to document the colorimetric changes.

Figure 5:
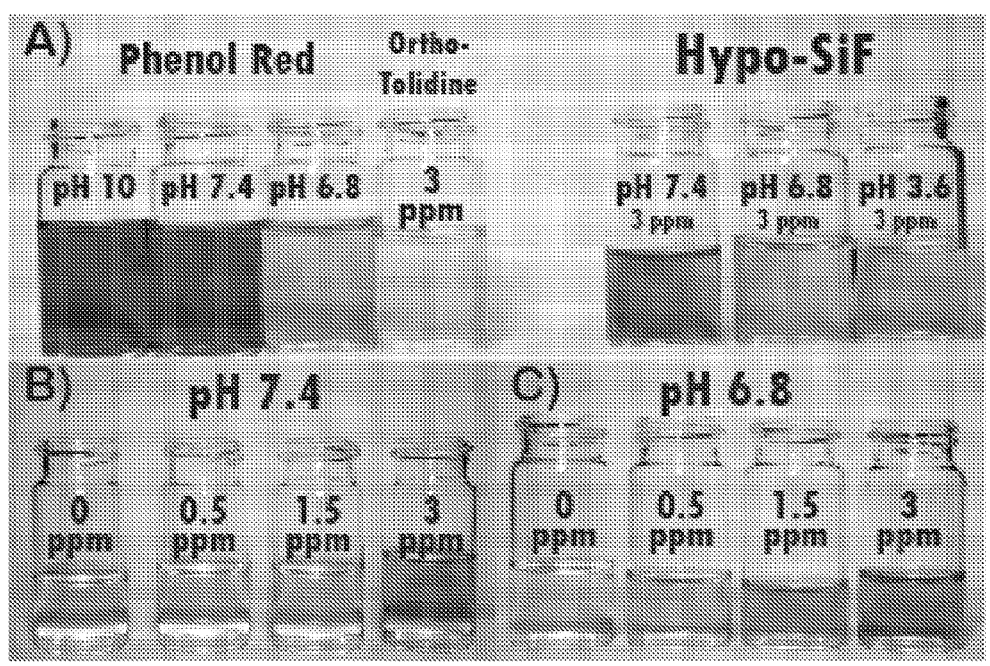
FIGS. 5A-C are photographs comparing the colorimetric response of a silaanthracene compound with the known indicators Phenol Red and ortho-Tolidine.

FIG. 5A summarizes the colorimetric response of compound 29 to 3 ppm solutions of HOCl compared to the colorimetric response of phenol red (a pH-only indicator) and orthotolidine (an HOCl-only indicator). FIGS. 5B and 5C summarize the simultaneous colorimetric detection for different concentrations of HOCl and pH measured from a sample solution formed by adding 200 μL of the stock solution to a 5 mL solution of HOCl, in which the sample solutions were buffered to pH levels of 7.4 and 6.8, respectively.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A compound of Formula (I):

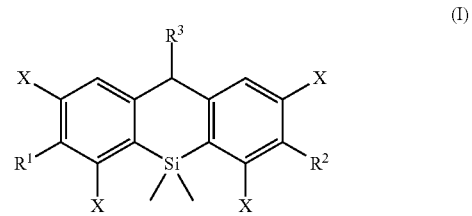

wherein:

X is selected from the group consisting of hydrogen and halogen;

$R^1$ is selected from the group consisting of amino and hydroxy;

$R^2$ is selected from the group consisting of amino, imino, hydroxy, and keto;

$R^3$ is selected from the group consisting of

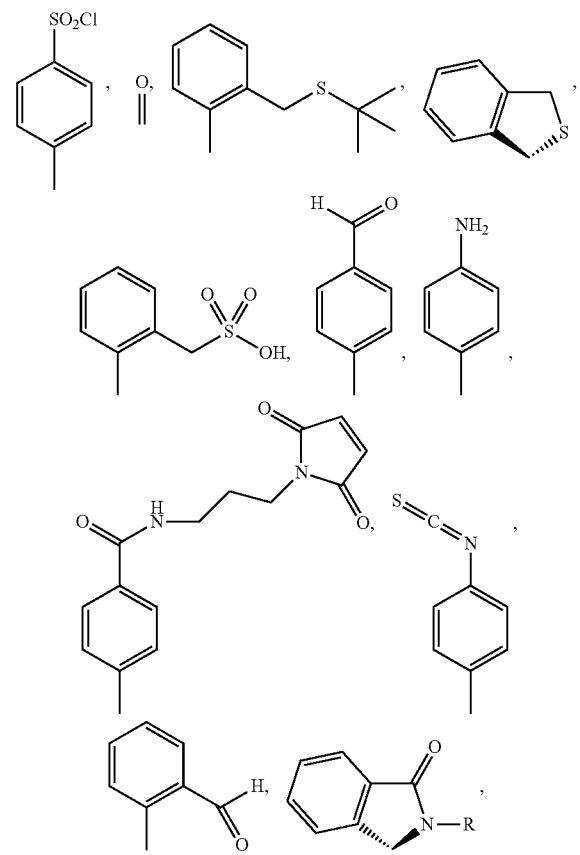

-continued

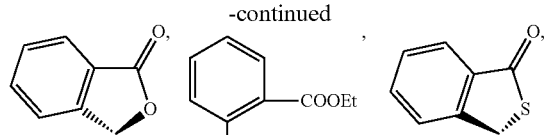

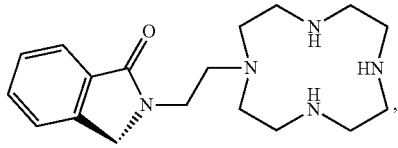

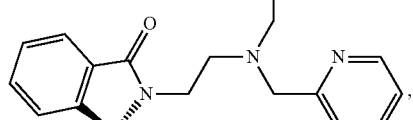

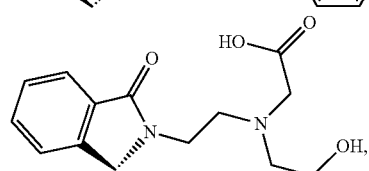

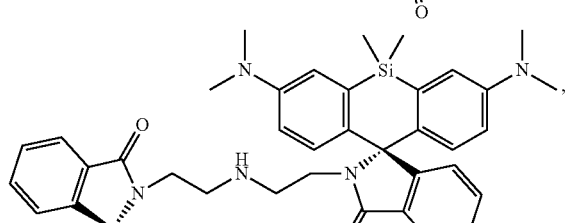

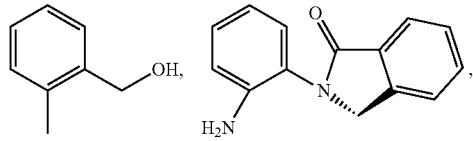

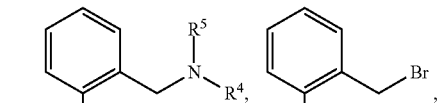

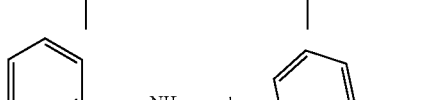

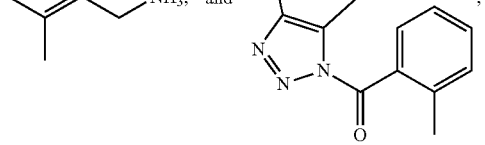

and wherein R, $R^4$ and $R^5$ are independently chosen from alkyls.

2. The compound of claim 1, wherein $R^1$ and $R^2$ are aminos.

3. The compound of claim 1, wherein $R^1$ is an amino and $R^2$ is an imino.

4. The compound of claim 1, wherein $R^1$ and $R^2$ are hydroxys.

5. The compound of claim 1, wherein $R^1$ is a hydroxy and $R^2$ is a ketone.

6. A chemical sensor/probe comprising Formula (I):

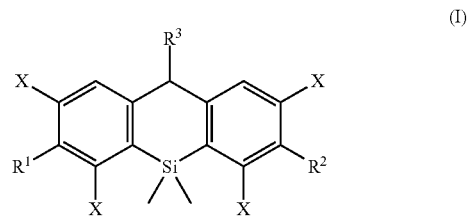

(I)

Wherein:

X is selected from the group consisting of hydrogen and halogen;

$R^1$ is selected from the group consisting of amino and hydroxy;

$R^2$ is selected from the group consisting of amino, imino, hydroxy, and keto;

$R^3$ is selected from the group consisting of

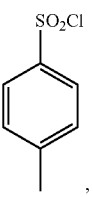 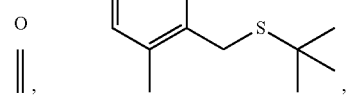 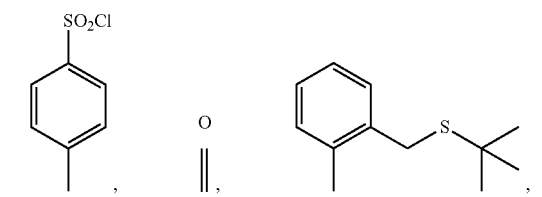

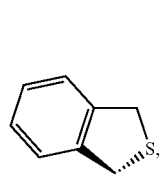 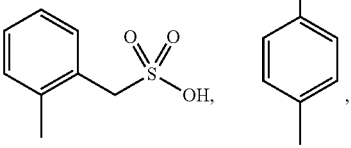

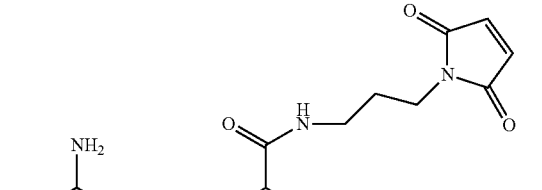

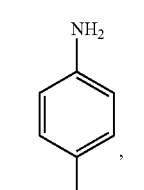 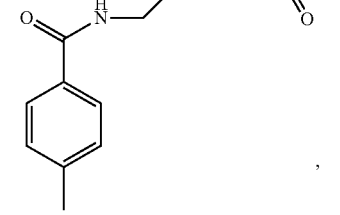

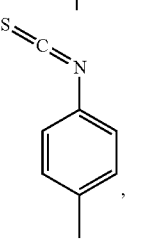 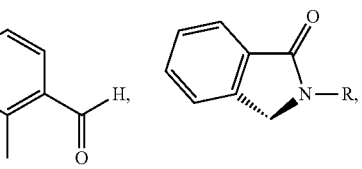

-continued

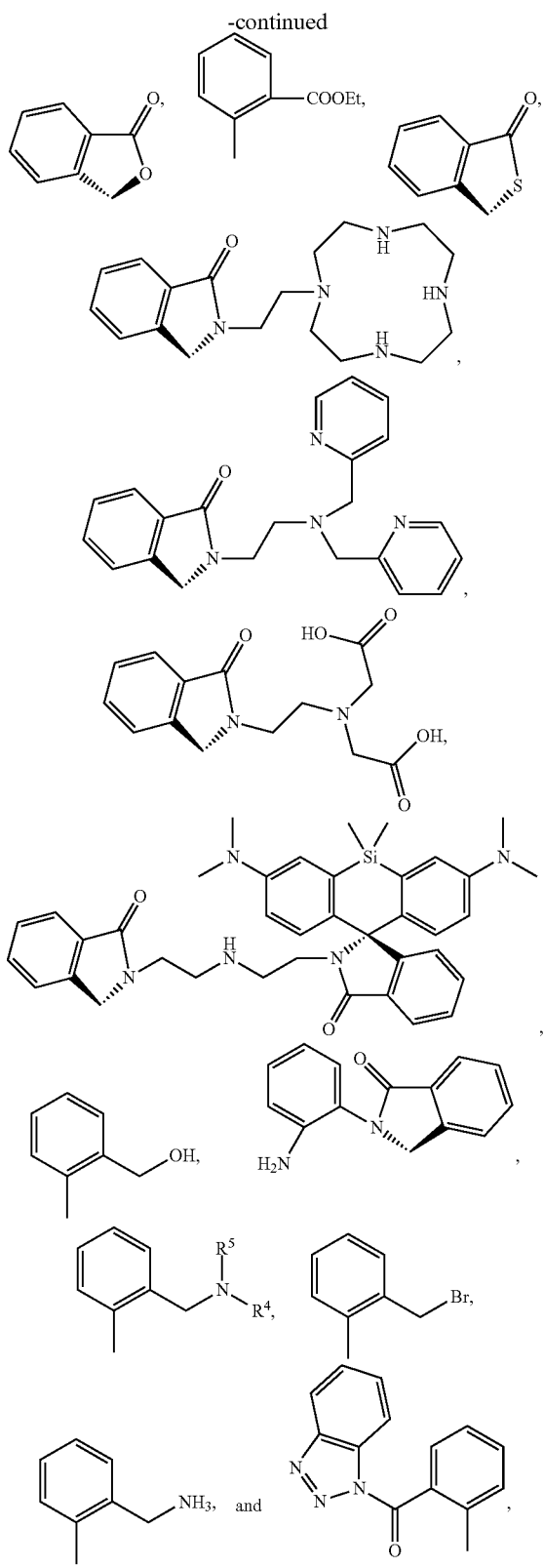

wherein R, R⁴ and R⁵ are independently chosen from alkyls;

wherein the chemical sensor/probe produces one or more analytically useful signals when contacted with at least one analyte; and wherein the one or more analytically useful signals are selected from the group consisting of absorption of light at one or more characteristic wavelengths ranging from about 570 nm to about 663 nm, emission of red or NIR light at one or more characteristic wavelengths in response to at least one excitatory light pulse delivered at a wavelength ranging from about 430 nm to about 655 nm, emission of light at a characteristic peak intensity ranging from about 40,000 a.u. to about 800,000 a.u. observed at a wavelength ranging from about 430 nm to about 663 nm, a color change in solution, and any combination thereof.

7. The composition of claim 6, wherein one or more analytically useful signals is a mathematical combination of two or more other signals of the one or more analytically useful signals, wherein the mathematical combination is selected from the group consisting of signal sums, signal differences, signal products, signal ratios, signal integrations, signal rates, and any combination thereof.

8. The composition of claim 7, wherein the chemical sensor/probe produces one signal when contacted with one analyte.

9. The composition of claim 7, wherein the chemical sensor/probe produces one signal when contacted with two or more analytes.

10. The composition of claim 7, wherein the chemical sensor/probe produces two or more signals when contacted with two or more analytes, wherein each of the two or more signals is associated uniquely with one of the two or more analytes.

11. The composition of claim 6, wherein the analyte is selected from the group consisting of a cell, a subcellular structure, a chemical compound, and a chemical condition.

12. A dye/tag comprising Formula (I):

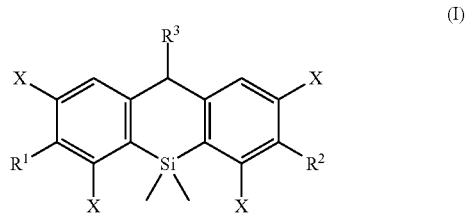

wherein

X is selected from the group consisting of hydrogen and halogen;

R¹ is selected from the group consisting of amino and hydroxy;

R² is selected from the group consisting of amino, imino, hydroxy, and keto;

R³ is selected from the group consisting of

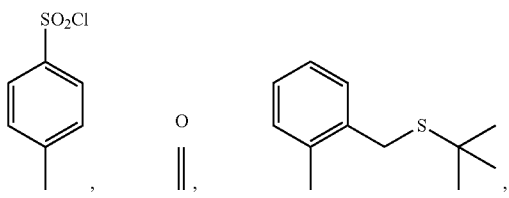

-continued

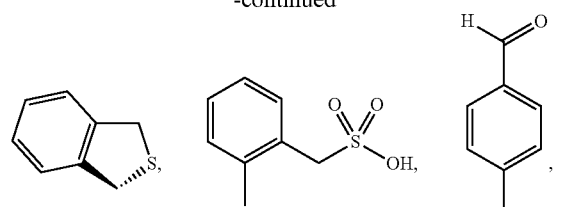
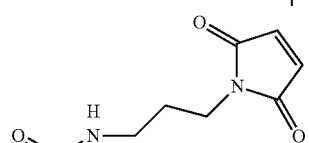
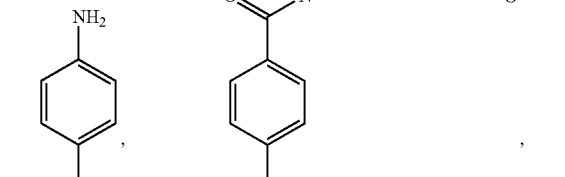
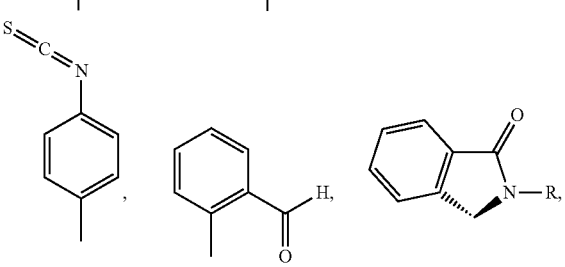
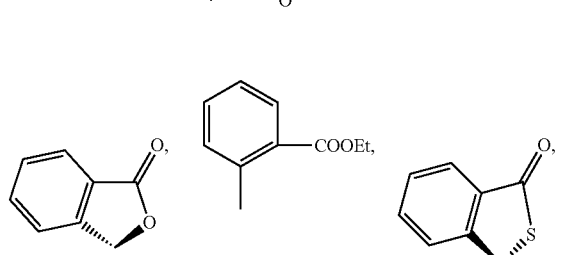
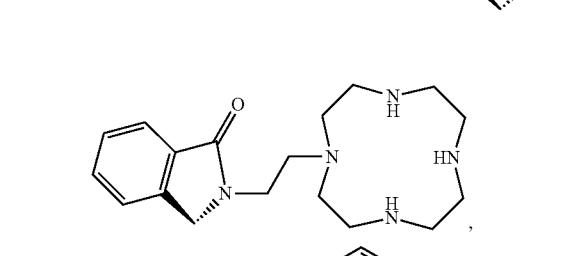
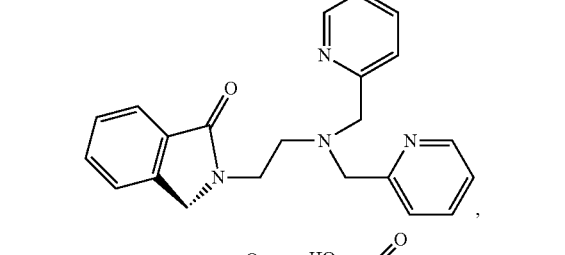
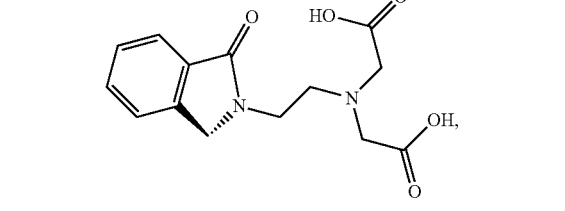

-continued

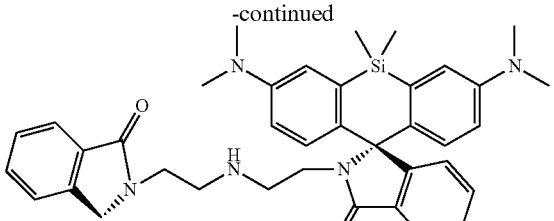
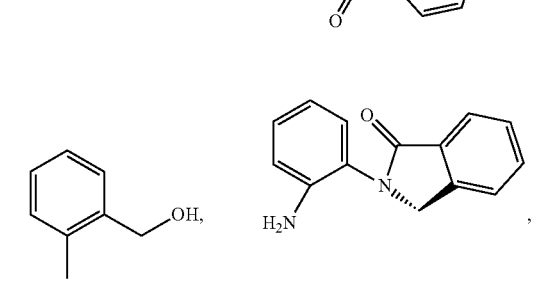
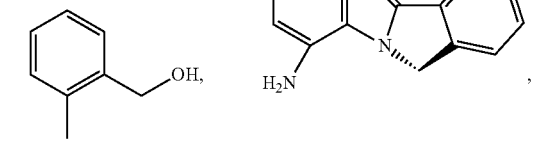
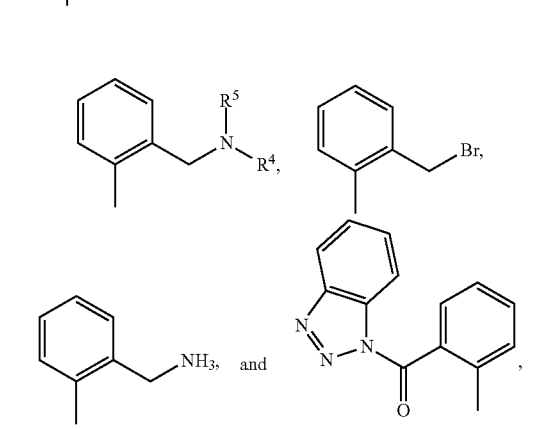

wherein the dye/tag is mixed with or attached to an entity, and one or more analytically useful signals produced by the dye/tag are monitored; and wherein the one or more analytically useful signals are selected from the group consisting of absorption of light at one or more characteristic wavelengths ranging from about 570 nm to about 663 nm, emission of red or NIR light at one or more characteristic wavelengths in response to at least one excitatory light pulse delivered at a wavelength ranging from about 430 nm to about 655 nm, emission of light at a characteristic peak intensity ranging from about 40,000 a.u. to about 800,000 a.u. observed at a wavelength ranging from about 430 nm to about 663 nm, a color change in solution, and any combination thereof.

13. The composition of claim 12, wherein the entity is selected from the group consisting of a peptide, a protein, a biomolecule, and a biological cell.

14. The composition of claim 12, wherein the one or more analytically useful signals are monitored continuously.

15. The composition of claim 14, wherein one or more analytically useful signals are used to track at least one movement of the entity.

16. The composition of claim 12, wherein the one or more analytically useful signals are monitored non-continuously.

17. The composition of claim 16, wherein the one or more analytically useful signals are used to track the location of the entity.

18. A compound of Formula (II):
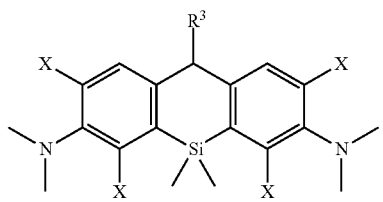
wherein:
X is selected from the group consisting of hydrogen and halogen;
R³ is selected from the group consisting of
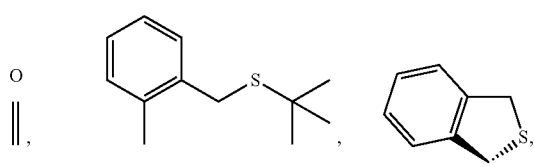
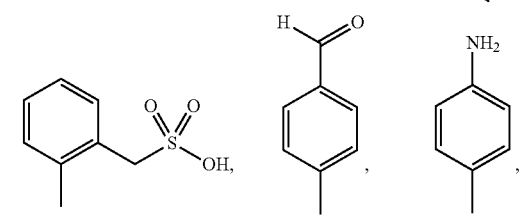
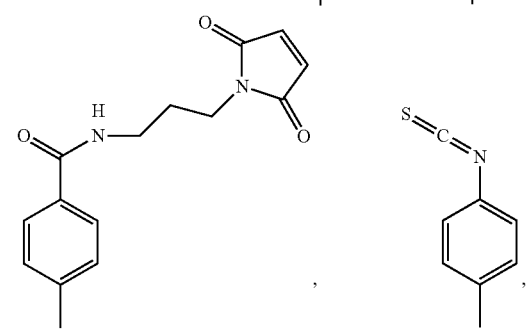
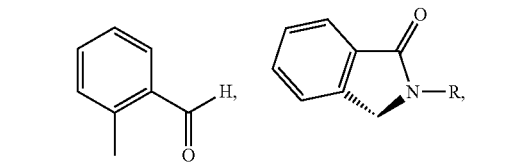
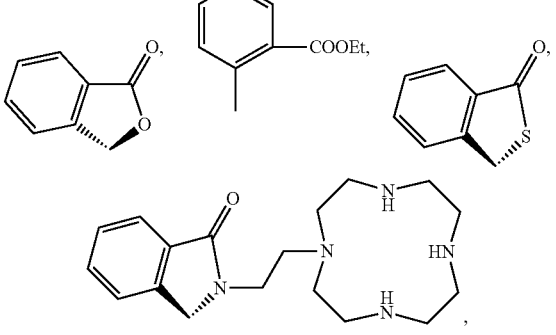
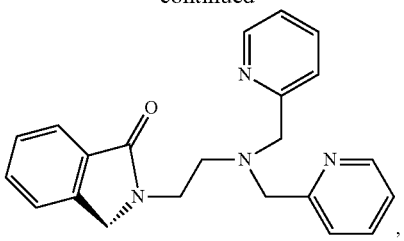
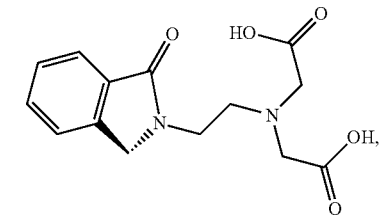
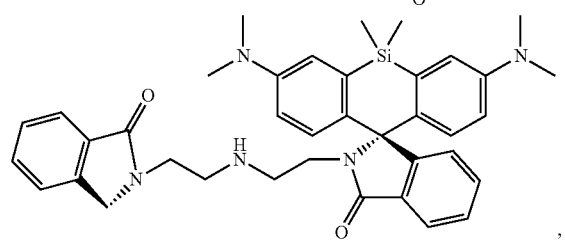
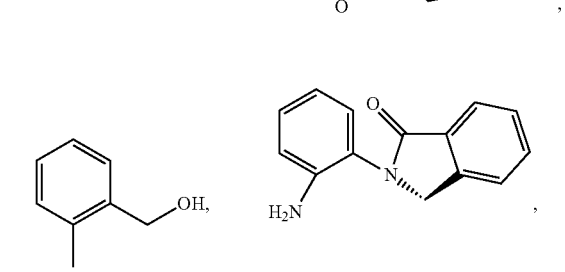
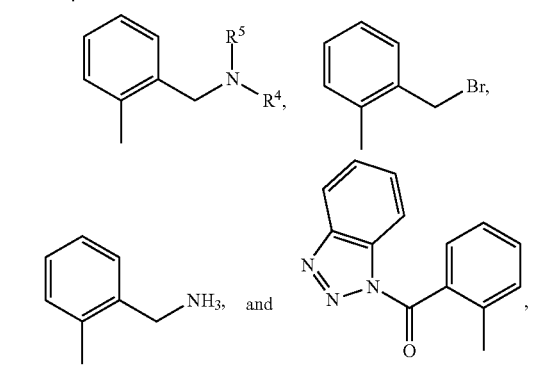
19. A chemical sensor/probe comprising Formula (II):
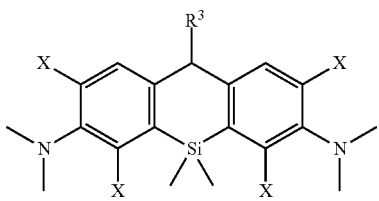
wherein X is selected from the group consisting of hydrogen and halogen;

$R^3$ is selected from the group consisting of

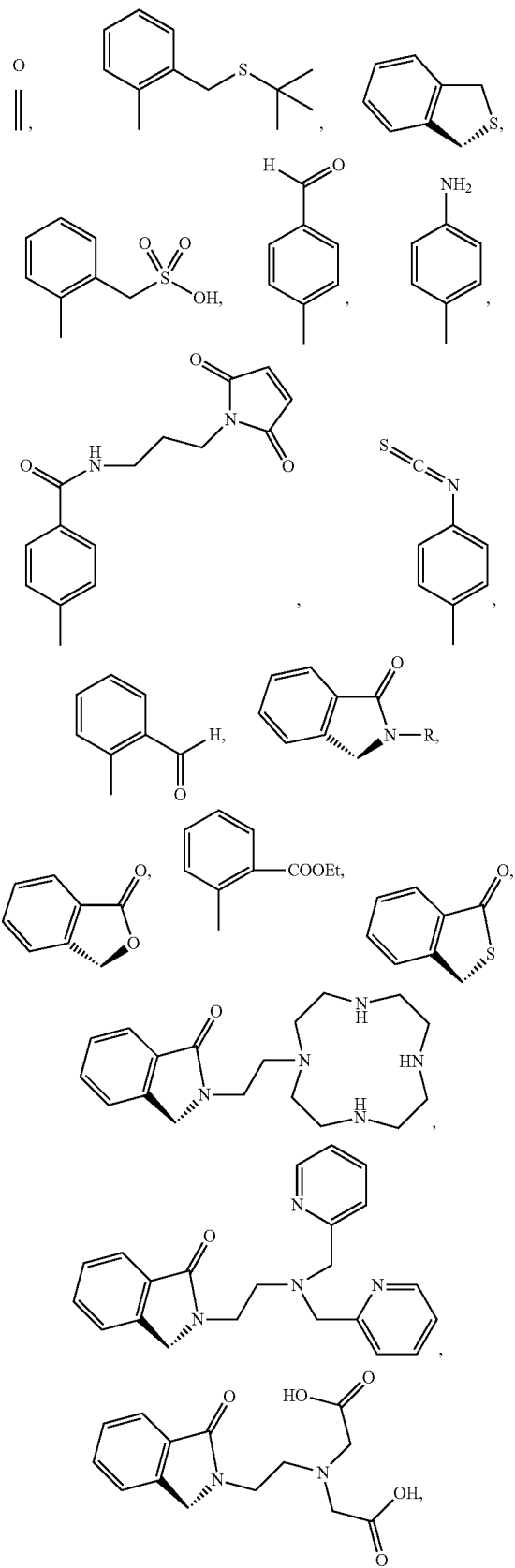

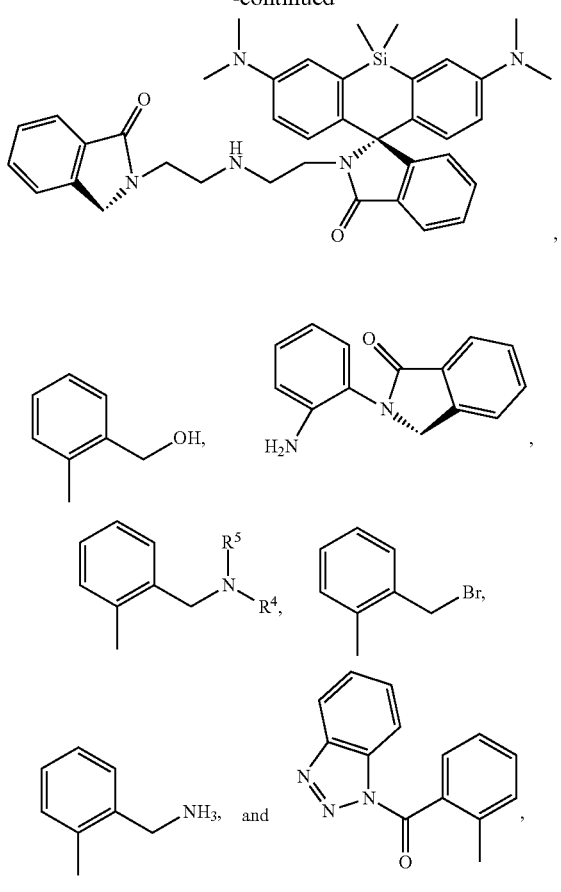

wherein the chemical sensor/probe produces one or more analytically useful signals when contacted with at least one analyte; and wherein the one or more analytically useful signals are selected from the group consisting of absorption of light at one or more characteristic wavelengths ranging from about 570 nm to about 663 nm, emission of red or NIR light at one or more characteristic wavelengths in response to at least one excitatory light pulse delivered at a wavelength ranging from about 430 nm to about 655 nm, emission of light at a characteristic peak intensity ranging from about 40,000 a.u. to about 800,000 a.u. observed at a wavelength ranging from about 430 nm to about 663 nm, a color change in solution, and any combination thereof.

20. A dye/tag comprising Formula (II):

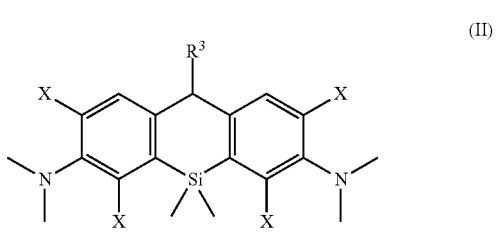

wherein X is selected from the group consisting of hydrogen and halogen; and

R³ is selected from the group consisting of

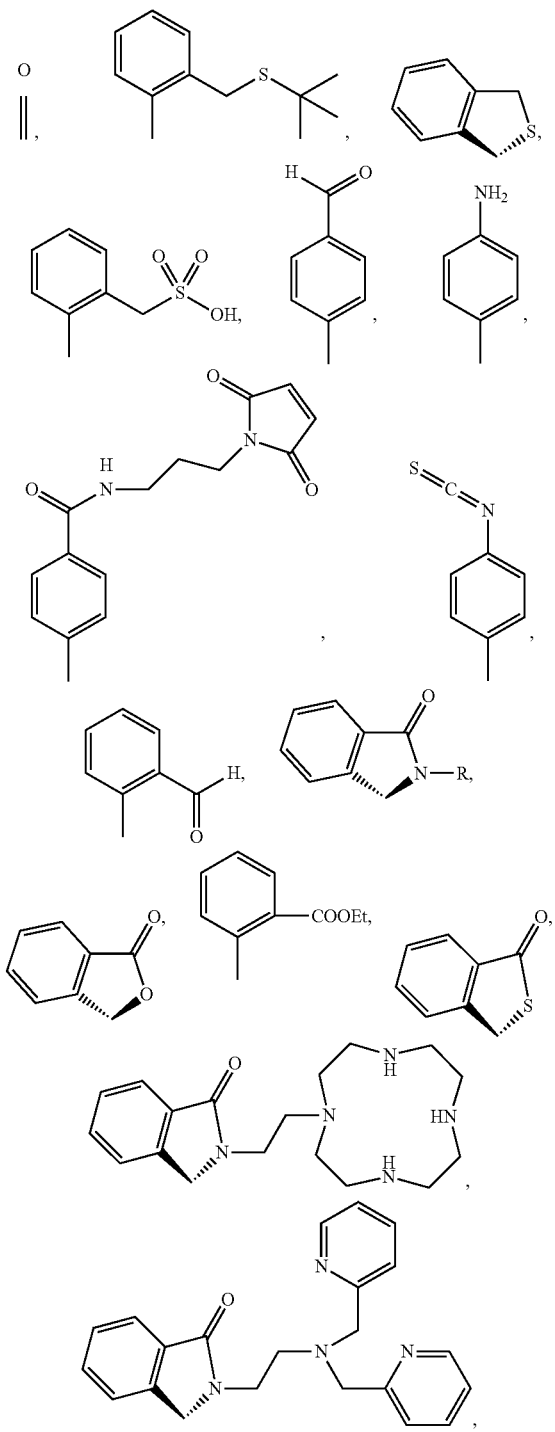

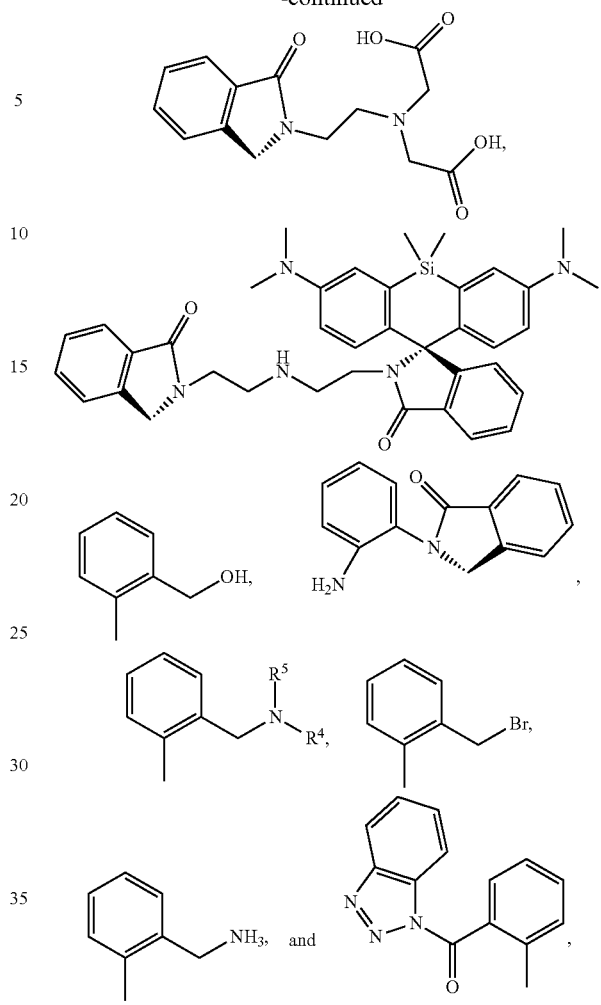

wherein the dye/tag produces one or more analytically useful signals when contacted with at least one analyte; and wherein the one or more analytically useful signals are selected from the group consisting of absorption of light at one or more characteristic wavelengths ranging from about 570 nm to about 663 nm, emission of red or NIR light at one or more characteristic wavelengths in response to at least one excitatory light pulse delivered at a wavelength ranging from about 430 nm to about 655 nm, emission of light at a characteristic peak intensity ranging from about 40,000 a.u. to about 800,000 a.u. observed at a wavelength ranging from about 430 nm to about 663 nm, a color change in solution, and any combination thereof.

\* \* \* \* \*